United States Patent
Masson

(10) Patent No.: US 8,532,806 B1
(45) Date of Patent: Sep. 10, 2013

(54) PROCESS FOR MANUFACTURE OF JOINT IMPLANTS

(76) Inventor: Marcos V. Masson, Houston, TX (US)

(*) Notice: Subject to any disclaimer, the term of this patent is extended or adjusted under 35 U.S.C. 154(b) by 473 days.

(21) Appl. No.: 12/794,932

(22) Filed: Jun. 7, 2010

(51) Int. Cl.
| G06F 19/00 | (2011.01) |
| G06F 17/10 | (2006.01) |
| A61F 2/06 | (2013.01) |
| A61F 2/44 | (2006.01) |
| B29C 59/00 | (2006.01) |
| B29C 45/14 | (2006.01) |

(52) U.S. Cl.
USPC ............ 700/98; 700/118; 700/163; 700/182; 703/7; 264/512; 264/515; 623/1.1; 623/17.16

(58) Field of Classification Search
USPC .... 700/98, 118, 163, 182; 703/7; 433/201.1; 345/418–421; 264/512, 515; 382/154; 623/1.1, 17.16, 18.11, 19.11–19.12
See application file for complete search history.

(56) References Cited

U.S. PATENT DOCUMENTS

| 4,550,450 A | | 11/1985 | Kinnett |
| 5,370,692 A | * | 12/1994 | Fink et al. ................. 128/898 |
| 5,593,448 A | | 1/1997 | Dong |
| 7,383,164 B2 | * | 6/2008 | Aram et al. .................. 703/7 |
| 7,967,868 B2 | * | 6/2011 | White et al. ............. 623/20.35 |
| 8,166,627 B2 | * | 5/2012 | Deffrennes .................. 29/558 |
| 8,246,680 B2 | * | 8/2012 | Betz et al. ................ 623/17.11 |
| 8,265,949 B2 | * | 9/2012 | Haddad .......................... 705/2 |
| 2003/0055507 A1 | | 3/2003 | McDevitt et al. |
| 2004/0133276 A1 | * | 7/2004 | Lang et al. ............... 623/14.12 |
| 2005/0203384 A1 | * | 9/2005 | Sati et al. ................... 600/426 |
| 2006/0069444 A1 | | 3/2006 | Deffenbaugh |
| 2006/0142657 A1 | * | 6/2006 | Quaid et al. .............. 600/424 |
| 2007/0219638 A1 | | 9/2007 | Jones et al. |
| 2007/0276501 A1 | * | 11/2007 | Betz et al. ................. 623/17.16 |
| 2009/0151736 A1 | * | 6/2009 | Belcher et al. ............. 128/898 |
| 2010/0292963 A1 | * | 11/2010 | Schroeder ...................... 703/1 |
| 2010/0324692 A1 | * | 12/2010 | Uthgenannt et al. ....... 623/20.35 |
| 2012/0065756 A1 | * | 3/2012 | Rubbert et al. ................ 700/98 |

* cited by examiner

*Primary Examiner* — Ramesh Patel
(74) *Attorney, Agent, or Firm* — Egbert Law Offices, PLLC

(57) ABSTRACT

An implant and process for manufacturing the implant for a joint of a patient comprises determining a dimension of a bone in the joint, generating a three-dimensional image of the bone, converting the image into a CAD model, determining a three-dimensional design for the implant according to the dimension of the bone, activating an electron beam melter, and additive-manufacturing the implant with the electron beam melter, the implant having a dimension equal to the dimension of the bone, the implant comprising a porous material. The porous material can be an osteoconductive material or an osteoinductive material or a combination thereof.

10 Claims, 5 Drawing Sheets

PROCESS FOR MANUFACTURE OF JOINT IMPLANTS

CROSS-REFERENCE TO RELATED APPLICATIONS

Not applicable.

STATEMENT REGARDING FEDERALLY SPONSORED RESEARCH OR DEVELOPMENT

Not applicable.

NAMES OF THE PARTIES TO A JOINT RESEARCH AGREEMENT

Not applicable.

INCORPORATION-BY-REFERENCE OF MATERIALS SUBMITTED ON A COMPACT DISC

Not applicable.

BACKGROUND OF THE INVENTION

1. Field of the Invention

The present invention relates to the repair of a fractured joints. Particularly, the present invention relates to the repair of the shoulder and the elbow. More particularly, the present invention relates to the repair of the glenoid of the shoulder and the coronoid of the elbow. More particularly, the present invention relates to the manufacture of implants for the repair of the glenoid and coronoid.

2. Description of Related Art Including Information Disclosed Under 37 CFR 1.97 and 37 CFR 1.98

Two commonly fractured joints of the human body are the shoulder and the elbow. The elbow is the joint between the humerus of the upper arm and the ulna and radius in the forearm. One of the most common fractures of the elbow involves the coronoid process of the ulna. In the most typical fracture pattern, the coronoid process is severed from the rest of the ulna along the bottom of the trochlear notch. Such fractures are often difficult to repair because the coronoid process is often shattered into many pieces and is very difficult to assemble and return to the original condition.

The shoulder is the joint between the glenoid and the humerus. The glenoid is a half-cup socket wherein the ball of the humerus sits. Glenoid and humerus fractures of the shoulder are hard to repair when the bones shatter into many pieces. Like the elbow, the glenoid or humerus of the shoulder can fracture into many pieces and be very difficult to assemble and return to their original condition. Additionally, anterior shoulder dislocation can involve the soft tissue structures of the labium and capsule and an anterior glenoid scapular bone fracture. The capsular injury can occur at the medial (glenoid rim), at the lateral capsular (Humeral-HALL) insertion only, or have a combined capsulolabral injury (Bankart lesion). When the bone fracture of an anterior shoulder dislocation involves more than 22% of the articular surface, recurrent shoulder dislocations and progressive arthritis often occur.

In both the shoulder and the elbow, if fractured pieces of the bones are salvageable, a surgeon can use screws to hold the shoulder bones or elbow bones in place while they heal. However, even when the shattered pieces heal, there can be bone loss and a loss of stability in the shoulder and elbow joints. A bone graft, such as an iliac crest bone graft fixation or a coracoid transfer (Laterjet/Bristow Procedure), can be used to strengthen the pieces of the fractured bones when they heal. Bone grafting falls into three general areas: osteogenic stimulation, osteoconductive stimulation and osteoinductive stimulation. Osteogenic stimulation is stimulation of bone growth at the fracture site by transplant of healthy, living bone cells from elsewhere in the body, such as portions of another bone or bone marrow. Osteoconductive stimulation uses orthobiologic materials such as ceramics, calcium sulfate compounds, calcium phosphate compounds, hydroxyapatite, deproteinized bone, corals, and polymers. These materials act as a scaffold between the pieces of the fractures bones on which bone cells grow to repair the shoulder and elbow fractures. Osteoinductive stimulation uses chemicals and proteins in the body to stimulate primitive bone stem cells to grow and mature at the fracture site.

A problem associated with bone graft methods that address recurrent dislocations due to bony defects in the shoulder is that said methods are technically difficult and cause post-traumatic arthritis. Thus, there is a need for methods for repair of bony defects of the shoulder that are less difficult and reduce the chance of post-traumatic arthritis.

Another problem associated with bone graft techniques is that even when bone growth is stimulated, the congruency and consistency of bony articular congruency can be affected. That is, the fractured pieces of bone can heal in an improper form due to an imperfect set by the surgeon and minute movements of the bone pieces and grafts during the healing period. Improper form leads to patient discomfort, joint instability over time, and even arthritis. Thus, there is a need to ensure proper form of the healing bones during the healing period.

An alternative to salvaging shattered and crushed elbow and shoulder bones is to remove the fractured pieces and use implants to repair the shoulder and elbow joints. However, a problem associated with implants is their material—implants are commonly made of materials biologically foreign to the human body. Thus, there is a need for implants that are not biologically foreign to the human body.

Various patents have issued relating to joint implants. For example, U.S. Patent Publication Serial No. 2006/0069444 describes an augmented glenoid implant that has a first component for attachment to a scapula. A first support surface on the first component cooperates with the glenoid fossa. A second surface of the implant is positioned adjacent a buttress formed in the glenoid fossa. A second component is removably secured to the first component. The second component has an articulating surface opposed to the assembly surface.

U.S. Patent Publication Serial No. 2003/0055507 describes a modular prosthesis for use with a shoulder implant. The prosthesis is attached to the bone by a stem that expands in a bone structure in response to the insertion of a pin. When the pin is inserted into the opening of the base and is fully engaged with the open top and hollow interior of the stem, an interference fit is created in the bone because the pin forces the stem to expand inside the void of the bone. This expansion creates a compressive mechanical lock of the prosthesis in the bone.

U.S. Pat. No. 5,593,448 discloses a glenoid implant that has affixation pegs thereon. The pegs are inserted, along with cement, into the holes formed on a surface of the scapula.

U.S. Pat. No. 4,550,450 discloses a shoulder prosthesis system. The articular surface of the humerus and the adjacent glenoid articular surface have a convex surface and a shallow trapezoidal fixation keel. The inferior aspect of the acromion is resurfaced with an acromial component for replacement of the acromial clavicular joint.

U.S. Patent Publication No. 2007/0219638 describes a prosthetic glenoid component for attachment to a scapula. The component has a one-piece bearing element having a concave lateral bearing surface for contact with the humeral head. An opposing relatively hard medial surface of the bearing element is provided for attachment to the scapula. The lateral surface is a soft low modulus concave lateral bearing surface that extends around the periphery of the bearing element and increases its thickness to provide a deformable rim to simulate the labium in an anatomical glenoid. The bearing element has a pair of affixation pegs which project from the medial face thereof.

The prior art reveals joint implants are readily available for repair of fractured joints; however, in practice, it is extremely difficult for an implant to simulate the unique contours of each human joint. Thus, when surgeons choose, or are forced, to use implants to repair shoulder and elbow joints, a compromise is made in that the patient is often fitted with an implant that does not exactly match anatomical contour of the patient's joint, thus lacking in congruency and consistency of bony congruency. Mismatched contours and a lack of congruency lead to a discomfort for patients and can lead to pain and joint instability over time. Thus, there is a need for an implant that better simulates the contour of the original shoulder and elbow joints for each individual patient and provides congruency and consistency of congruency which reduces patient discomfort and increases joint stability.

It is an object of the present invention to manufacture an implant of the elbow and should that better matches the contour of a patient's joint anatomy.

It is another object of the present invention to design a joint implant that is functional, manufactured and solves the problem of joint instability.

It is another object to repair shoulder and elbow fractures using biologically native materials.

It is another object to increase should stability of the glenoid using an implant that anatomically matches the other bones of a patient's injured shoulder.

It is another object to increase elbow stability of the caranoid using an implant that anatomically matches the other bones of a patient's injured elbow.

It is another object to establish a small implant bone that is able to integrate with cancellous bone and withstand significant forces exceeding 400 N (Newtons) and remain stable through repeated use.

It is another object to build a glenoid implant.

It is another object to improve the quality of life of individuals having severely unstable and recurrent anterior shoulder dislocations.

It is another object to product joint implants that are dense, void-free, and extremely strong.

It is another object to avoid morbidity of the fracture site of the bones in the joint.

It is another object to provide better joint congruity with a smooth articular surface for the joint.

It is another object to avoid post-traumatic arthritis in the elbow and shoulder.

These and other objects and advantages of the present invention will become apparent from a reading of the attached specification and appended claims.

BRIEF SUMMARY OF THE INVENTION

The present invention is an implant for a joint of the human body and a process of manufacturing the implant.

The process for manufacturing an implant for a joint of a patient comprises determining a dimension of a bone in the joint, generating a three-dimensional image of the bone, converting the image into a CAD model, determining a three-dimensional design for the implant according to the dimension of the bone, activating an electron beam melter, and additive-manufacturing the implant with the electron beam melter, the implant having a dimension equal to the dimension of the bone, the implant comprising a porous material. The porous material can be an osteoconductive material or an osteoinductive material. The process also includes the steps of converting the dimension to a format used in image-reconstruction software before the step of generating a three-dimensional image, determining a method of fixation of the implant in the patient, determining a location of fixation of the implant in the patient, and designing instrumentation required for fixation of the implant in the patient.

The step of determining a dimension comprises scanning a fractured area of the joint with a CT scanner, and performing a three-dimensional reconstruction of the fractured area. The dimension comprises a dimension of an anterior face of the bone, a curvature of a neck of the bone, and a total volume of an amount of the bone equal to 25% of the anterior face of the bone, where the bone is a glenoid.

The step of performing a three-dimensional reconstruction comprises calculating an arc of a face of the bone, calculating a depth of a neck of the bone, calculating a superior/inferior value of the bone, and calculating an anterior/posterior value of the bone, where the bone is a glenoid.

The step of determining a three-dimensional design for the implant comprises the steps of determining a force crossing 25% of an anterior of the bone, determining a distribution of forces of the implant by finite element analysis, and determining an area of potential failure of the implant. The step of determining a force comprises calculating a density of a cancellous bone at the face of the bone, and determining a normal humeral translational moment. The bone can be a glenoid.

The implant is manufactured by additive-manufacturing with an electron beam melter, and the implant comprises a dimension equal to the dimension of a fractured bone of the joint, and a porous material. The porous material can be osteoconductive or osteoinductive.

DETAILED DESCRIPTION OF THE INVENTION

Figure 1:
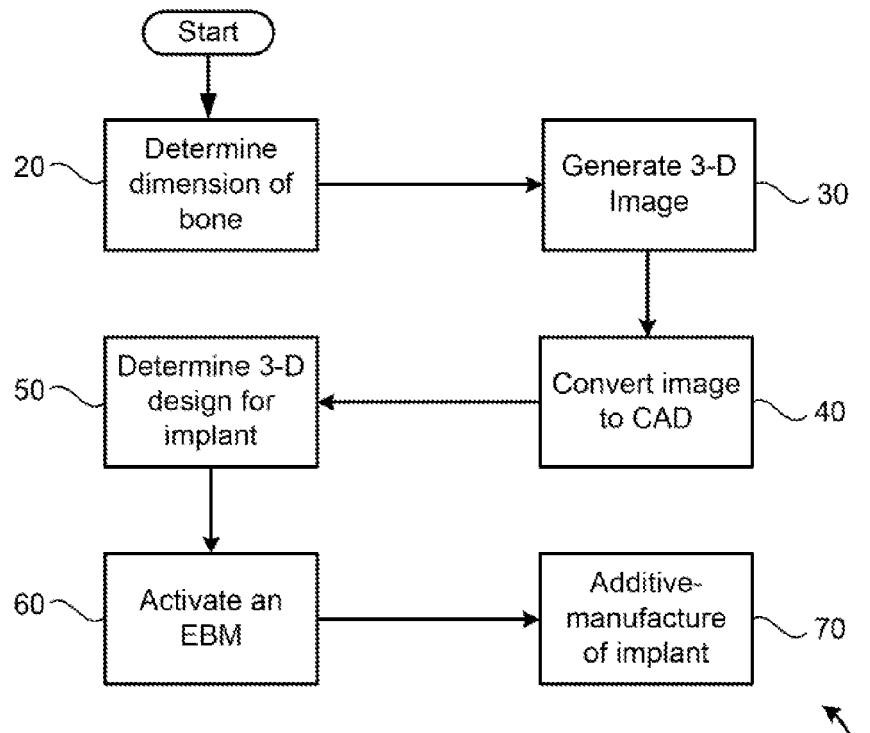
FIG. 1 shows a flow diagram of the preferred embodiment of the disclosed process for manufacturing a joint implant.

Referring to FIG. 1, there is shown a flow diagram of the preferred embodiment of the disclosed process 10 for manufacturing a joint implant. To begin the process 10, a doctor must determine that a patient has a fracture and is in need of an implant in the joint. The joint can be a shoulder or an elbow. The process 10 beings at process block 20, where a dimension of a bone in the joint is determined. The dimensions of the bone are the dimensions necessary for manufacturing the implant according to the disclosed process 10. For example, when manufacturing an implant for a fractured glenoid of the shoulder, the dimensions of the anterior face of the glenoid, the curvature of the neck of the glenoid, and a total volume of an amount of the glenoid equal to 25% of the anterior face of the glenoid are determined. The dimensions are determined through steps discussed below in FIG. 3.

After a dimension is determine in process block 20, activity proceeds to process block 30, where a three-dimensional image of the bone is generated. After a three-dimensional image of the bone is generated in process block 30, activity proceeds to process block 40 where the image is converted into a CAD model for manipulation and display in AUTOCAD. After the image is converted into a CAD model in process block 40, activity proceeds to process block 50, where a three-dimensional design for the implant is determined according to the dimension of the bone. The three-dimensional design made in process block 50 has various parameters tested and determine as described in FIG. 4. After the three-dimensional design for the implant is made in process block 50, activity proceeds to process block 60, where an electron beam melter (EBM) is activated in order to manufacture the implant. Electron beam melting is a technology for manufacturing objects, and in the case of the disclosed method 10, implants and fixation instruments. In electron beam melting, an electron beam is directed into a powder, where the powder is preferably comprised of materials that make a porous, osteoconductive/osteoinductive implant and fixation instrument after electron beam melting. The electron beam has an extremely high temperature; thus, the materials in the powder melt upon contact, and the objects made in the EBM are made from the inside out by melting and cooling layer upon layer of the object upon itself. The temperature of the electron beam can be adjusted by adjusting the intensity and magnetic fields that control the direction and diameter of the electron beam. Making an implant and fixation instrument by electron beam melting ensures the density is constant, the purity of material is high, and the contour of the object produced can be controlled in high levels of detail. In process block 60, the three-dimensional design made in process block 50 is sent to the EBM, and the EBM is readily compatible to accept and manufacture an implant according to a three-dimensional CAD model. After the EBM is activated in process block 60, activity proceeds to process block 70, where the implant is additive-manufactured with the EBM. Additive-manufacturing is the name for the process of manufacturing objects by melting layer upon layer of a material upon one another to form an object from the inside out. The term "additive" is in contrast to other manufacturing technologies that are "subtractive", such as machining of a block of material into an object with a lathe. The EBM additive-manufactures the implant to have a dimension equal to the dimension of the bone. In practice, there can be many dimensions of the implant that are additive-manufactured to equal the dimensions of the bone. As stated above, for example, the preferred dimensions for a glenoid of the should are: the dimensions of the anterior face of the glenoid, the curvature of the neck of the glenoid, and a total volume of an amount of the glenoid equal to 25% of the anterior face of the glenoid are determined.

Figure 2:
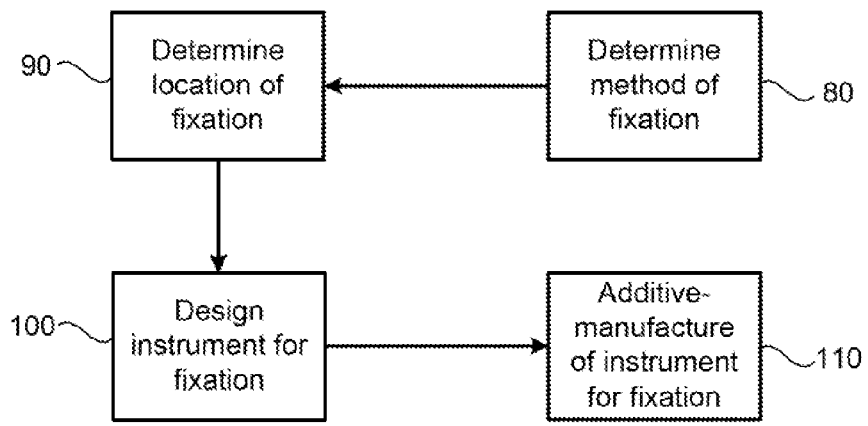
FIG. 2 shows a flow diagram of the manufacture of the instrument for fixation of the joint implant.

Referring to FIG. 2, there is shown a flow diagram of the manufacture of the instrument for fixation of the joint implant. In the preferred process 10, activity proceeds to process block 80, where a method of fixation of the implant in the patient is determined. For example, a surgeon can determine to fix the implant by using a screw as the method of fixation. After the method of fixation of the implant is determined in process block 80, activity proceeds to process block 90, where a location of fixation of the implant in the patient is determined. The location is determined by examining the patient's bone area in order to ascertain the precise location in which to affix the implant according to the chosen method of fixation. After the location of the implant is determined in process block 90, activity proceeds to process block 100, where the instrumentation required for fixation of the implant in the patient is designed. In the example of the screw, the size, diameter, length, threads, curvature, and contour are all properties of the screw that can be designed in order to additive-manufacture a custom screw (instrument of fixation). Other fixation instruments may have other or additional properties that can be designed. Once the instrument of fixation is designed in process block 100, activity proceeds to process block 110, where the instrument of fixation is additive-manufactured by an EBM. According to the disclosed process 10, any instrument of fixation, such as a screw, is additive-manufactured with an EBM. Preferably, the material of the screw is porous, and the porous material is osteoconductive, osteoinductive, or a combination thereof.

Figure 3:
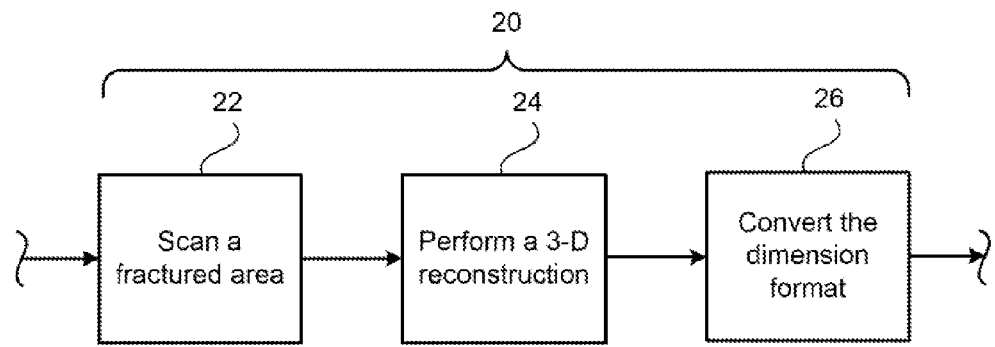
FIG. 3 shows a flow diagram for the step of determining a dimension of the bone.

Referring to FIG. 3, there is shows a flow diagram of sub-steps for the step of determining a dimension of bone in process block 20. The sub-steps include the steps of scanning a fractured area of the joint with a CT scanner in process block 22, performing a three-dimensional reconstruction of the fractured area in process block 24, and converting the dimension to a format used in image-reconstruction software in process block 26. The step of converting the dimension to a format is performed before the step of generating a three-dimensional image of process block 30 shown in FIG. 1.

Figure 4:
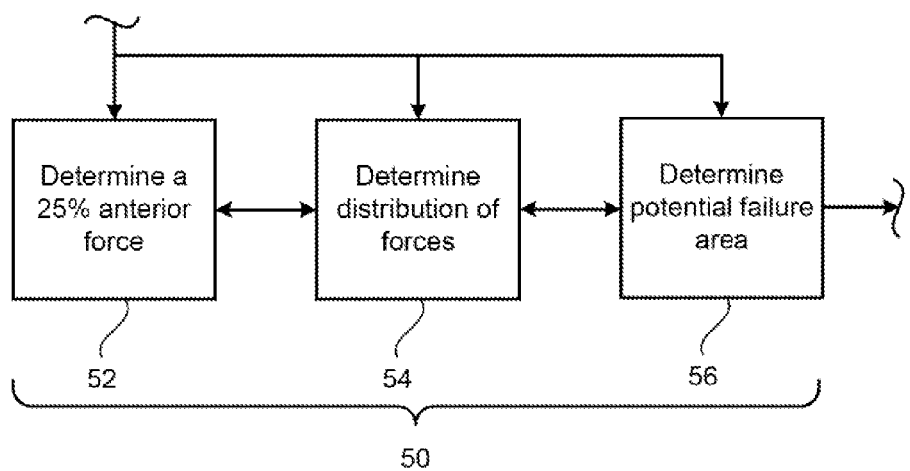
FIG. 4 shows a flow diagram for the step of determining a three-dimensional design for the implant.

Referring to FIG. 4, there is shown a flow diagram of the step of determining a three-dimensional design for the implant of process block 50. The step of determining a three-dimensional design shown in process block 50 includes the steps of determining a force crossing 25% of an anterior of the bone shown in process block 52, determining a distribution of forces of the implant by finite element analysis shown in process block 54, and determining an area of potential failure of the implant shown in process block 56. The arrows in FIG. 4 show activity flows in all direction so that process blocks 52, 54, and 56 can be performed in any order during the step of determining a three-dimensional design of the implant for process block 50 during the process 10.

Figure 5:
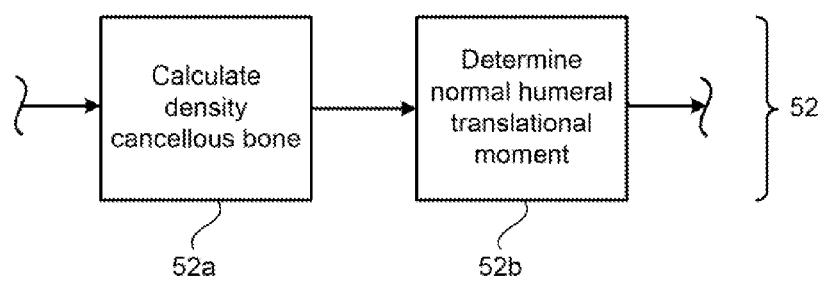
FIG. 5 shows a flow diagram of the step of determining a 25% anterior force.

Referring to FIG. 5, there is shown a flow diagram for the step of determining a 25% anterior of process block 52. The step in process block 52 has several sub-steps, which include calculating a density of a cancellous bone at the face of the bone in process block 52a, and determining a normal humeral-translational moment in process block 52b. Density of cancellous bone is calculated to allow for design adjustments of the implant and fixation instruments so as to allow the implant and fixation instrument to better integrate with the cancellous bone. The normal humeral-translational moment is determined so that forces occurring at the joint of the fracture site can be accounted for in the design of the implant and fixation instrument.

Figure 6:
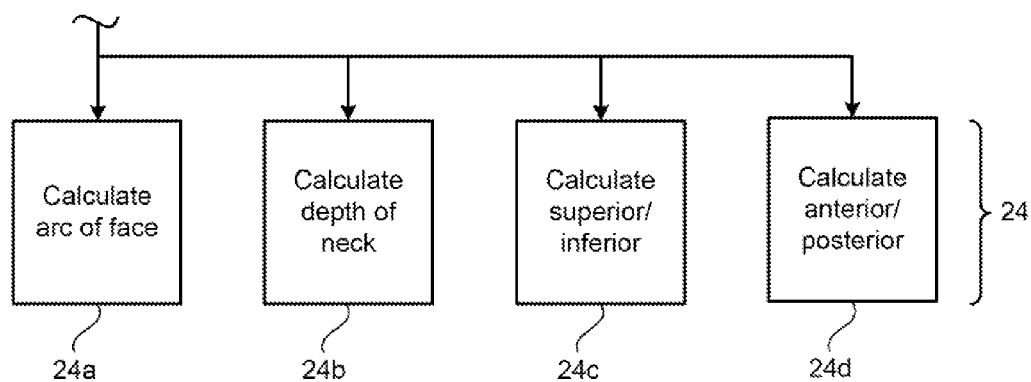
FIG. 6 shows a flow diagram for the step of performing a three-dimensional reconstruction.

Referring to FIG. 6, there is shown a flow diagram of sub-steps for the step of performing a three-dimensional reconstruction in process block 24 of FIG. 3. The sub-steps include the steps of calculating an arc of a face of the bone in process block 24a, calculating a depth of a neck of the bone in process block 24b, calculating a superior/inferior value of the bone in process block 24c, and calculating an anterior/posterior value of the bone in process block 24d. The arrows in FIG. 6 indicate the steps 24a, 24b, 24c, 24d can be done in any order needed to complete the calculation and to perform a three-dimensional reconstruction of the bone in process block 24. The values calculated in process block 24a, 24b, 24c, and 24d are particularly useful for a three-dimensional reconstruction of a glenoid of a should. Additional or alternative values can be calculated for different bones in the various joints application in the preferred process 10.

In the preferred process 10 shown in FIGS. 1 to 6, the implant is formed at least partially from a porous material. The porous material can be an osteoconductive material, an osteoinductive material, or a combination thereof. Preferably, the implant is formed entirely of a osteoconductive or osteoinductive material. An implant formed entirely of osteoconductive material will stimulate bone growth and strength by serving as a scaffold on which bone cells can grow. As bone cells grow, the implant will have biologically native materials therein, which is an advantage for strength and biological stability over implants formed merely of biologically foreign materials. An implant formed of osteoinductive material will stimulate bone growth and strength by inducing the patient's body to generate new and healthy bone cells. Like the osteoconductive implant, an osteoinductive implant will have biologically native materials therein having the same advantages. An implant the is both osteoconductive and osteoinductive will have a scaffold on which bone can grow and also induce bone growth. A combination implant that acts as a scaffold and also generates bone growth has the advantage of stimulating native material growth and having biologically native materials formed therein.

Figure 7:
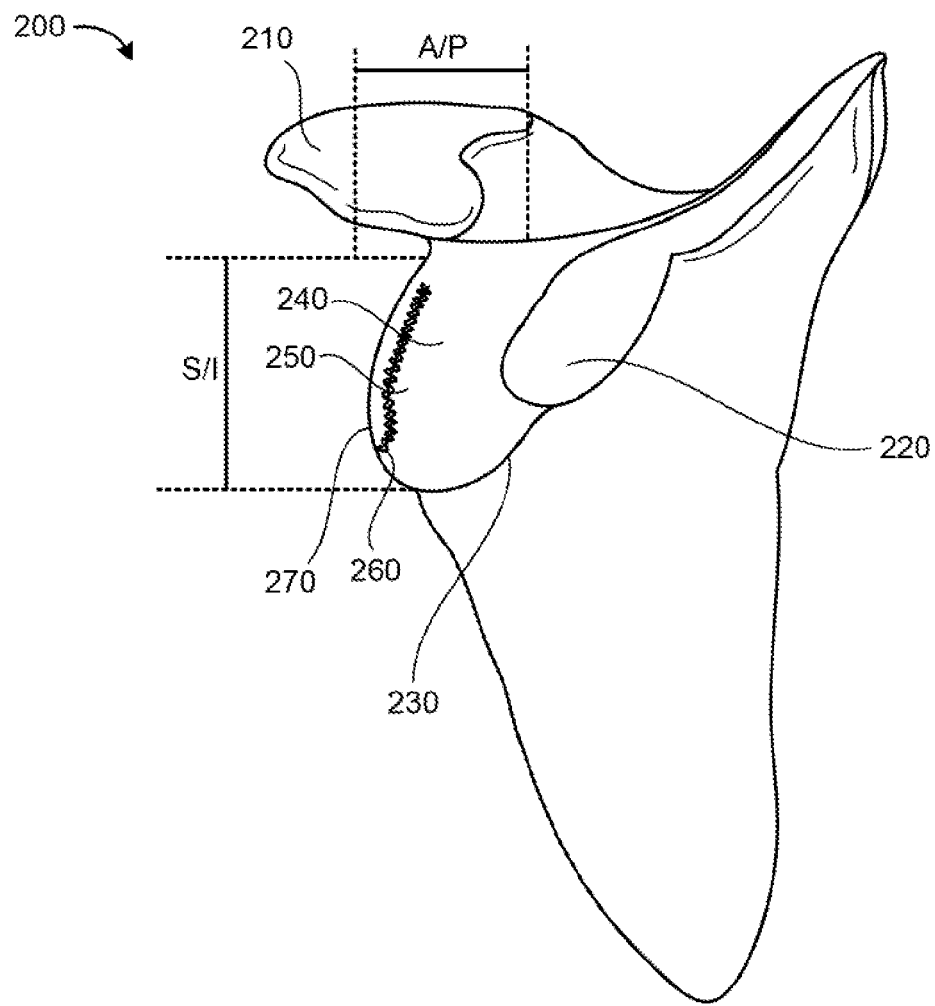
FIG. 7 shows a perspective view of a three-dimensional reconstruction of a fractured area of a shoulder from a human patient.

Referring to FIG. 7, there is shown a perspective view of a three-dimensional reconstruction 200 of a shoulder of a patient using the disclosed method. The shoulder has a coracoid process 220, acromion 210, and glenoid 250. The glenoid 250 has a neck 230 and a face 240. The curvature of the neck 230 is measured in the disclosed process. A fracture 260 can be seen in the anterior face 270 of the glenoid 250. Dimensions of the glenoid 250 that are measured include a dimension of the anterior face 270, a curvature of the neck 230 and a total volume of an amount of the glenoid 250 that is equal to 25% of the anterior face 250. For three-dimensional reconstruction, the value of the superior/inferior of the glenoid 250 is calculated and indicated in FIG. 7 by the term "S/I". The value of the anterior/posterior of the glenoid 250 is calculated and indicated in FIG. 7 by the term "A/P". An arc of the face 240 of the glenoid 250 is also calculated along with a depth of the neck 230 of the glenoid.

Figure 8:
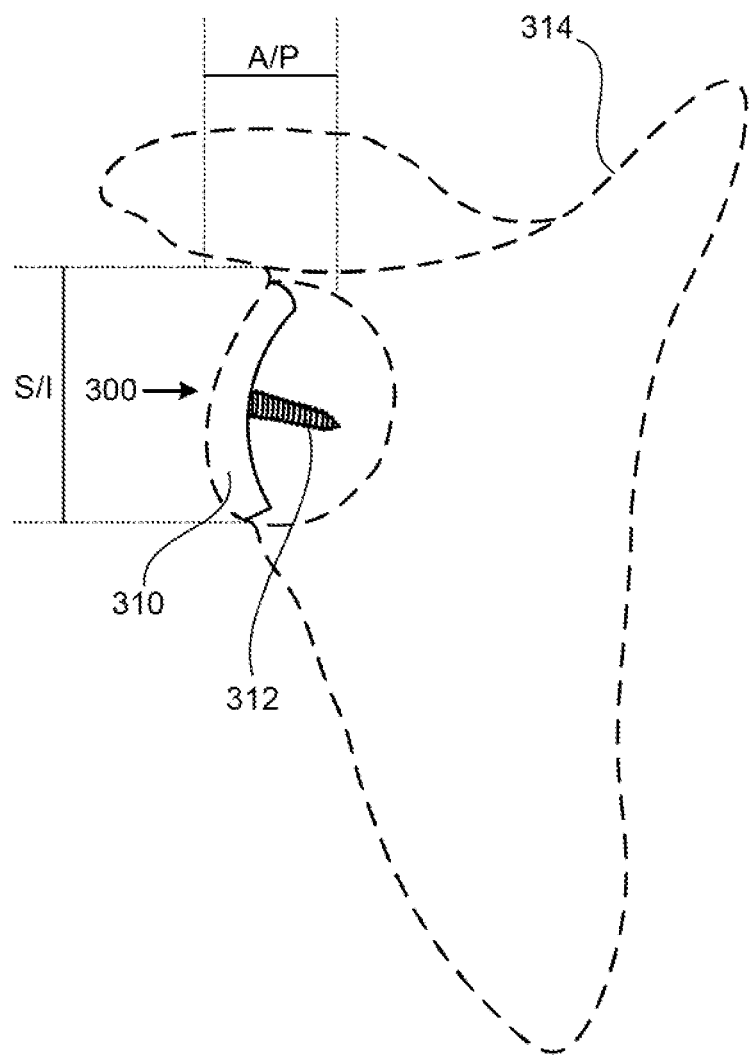
FIG. 8 shows a perspective view of an implant additive-manufactured according to the dimensions of the shoulder in FIG. 7 and according to the disclosed method.

Referring to FIG. 8, there is shown a perspective view of the implant 300 made according to the preferred disclosed method. The implant 300 is matched to the contour and continuity of contour of the anterior face 270 of the patient's glenoid 250 that is shown with a fracture 260 in the three-dimensional reconstruction shown in FIG. 7. That is, the implant 300 is manufactured for a glenoid that has the same "S/I", "A/P", and other properties stated above as the original bone before fracture. The implant 300 is affixed to the original bone 314 (shown in dotted and dashed lines) of the patient with a screw 312. The screw 312 is additive manufactured with an EBM and made of the same material as the implant 300. Each screw, or screws, can be custom designed for each patient according to the calculated values and dimensions determined by the preferred disclosed process 10.

The implant 300 is made of a porous material 310 that stimulates bone growth and shortens and improves healing. The porous material 310 is osteoconductive or osteoinductive. The implant 300 was manufactured by additive-manufacturing with an electron beam melter, which makes the implant 300 extremely strong. Moreover, the screw 12 was manufactured by additive-manufacturing with an EBM. Additive-manufacturing with an EBM has the advantages of being completed very quickly, uses a minimal amount of materials to build the implants and fixation instruments.

With the disclosed method 10, the implant 300 and screw 312 can be custom-designed for a patient so that the screw 312 and implant 300 match the unique contours and continuity of contour of the unique patient. Additionally, the materials of the implant 300 and screw 312 can be chosen to promote faster and stronger bone growth for the joint. The implant 300 and screw 312 are dense, void-free, and extremely strong when made according to the disclosed process 10. The implant 300 and screw 312 integrate with cancellous bone and withstand significant forces exceeding 400 N (Newtons) and remain stable through repeated use.

The foregoing disclosure and description of the invention is illustrative and explanatory thereof. Various changes in the details of the illustrated construction can be made within the scope of the appended claims without departing from the true spirit of the invention. The present invention should only be limited by the following claims and their legal equivalents.

I claim:

1. A process for manufacturing an implant for a joint of a patient comprising:
   determining a dimension of a bone in the joint;
   generating a three-dimensional image of the bone;
   convening the image into a CAD model;
   determining a three-dimensional design for the implant according to the dimension of the bone;
   activating an electron beam melter; and
   additive-manufacturing the implant with the electron beam melter, the implant having a dimension equal to the dimension of the bone, the implant comprising a porous material.

2. The process of claim 1, wherein the porous material is an osteoconductive material.

3. The process of claim 1, wherein the porous material being is an osteoinductive material.

4. The process of claim 1, wherein the step of determining a dimension comprises:
   scanning a fractured area of the joint with a CT scanner; and
   performing a three-dimensional reconstruction of the fractured area.

5. The process of claim 4, wherein the step of determining a dimension further comprises:
   converting the dimension to a format used in image-reconstruction software before the step of generating a three-dimensional image.

6. The process of claim 1, further comprising:
   determining a method of fixation of the implant in the patient; and
   determining a location of fixation of the implant in the patient.

7. The process of claim 6, further comprising:
   designing instrumentation required for fixation of the implant in the patient.

8. A process for manufacturing an implant for a joint of a patient, the process comprising:
   determining a dimension of a bone in the joint, said dimension being a dimension of an anterior face of the bone and a curvature of the neck of the bone and a total volume of an amount of the bone and a total volume of the an amount of the bone equal to 25% of the anterior face of the bone;
generating a three-dimensional image of the bone;
converting the image into a CAD model;
determining a three-dimensional design for the implant according to the dimension of the bone;
activating an electron beam melter; and
additive-manufacturing the implant with the electron beam inciter, the implant having a dimension equal to the dimension of the bone, the implant comprising a porous material.

9. The process of claim 8, the bone being a glenoid.

10. A process for manufacturing an implant for a joint of a patient, the process comprising:
determining a dimension of a bone in the joint, the bone being a glenoid;
generating a three-dimensional image of the bone;
converting the image into a CAD model;
determining a three-dimensional design for the implant according to the dimension of the bone, wherein the step of determining the three-dimensional design comprises:
determining a force crossing 25% of an anterior of the bone;
determining a distribution of forces of the implant by a finite element analysis, wherein the step of determining the distribution of forces comprises:
calculating a density of cancellous bone at the face of the bone; and
determining a normal humeral translational moment; and
determining an area of potential failure of the implant;
activating an electron beam melter; and
additive-manufacturing the implant with the electron beam melter, the implant having a dimension equal to the dimension of the bone, the implant being a porous material.

* * * * *